United States Patent [19]

Ivankovits et al.

[11] Patent Number: 5,028,724

[45] Date of Patent: Jul. 2, 1991

[54] SYNTHESIS OF VOLATILE FLUORINATED AND NON-FLUORINATED METAL-BETA-KETONATE AND METAL-BETA-KETOIMINATO COMPLEXES

[75] Inventors: John C. Ivankovits, Northampton; David A. Bohling, Emmaus; John A. T. Norman, Whitehall, all of Pa.; David A. Roberts, Carlsbad, Calif.

[73] Assignee: Air Products and Chemicals, Inc., Allentown, Pa.

[21] Appl. No.: 502,092

[22] Filed: Mar. 30, 1990

[51] Int. Cl.$^5$ .................. C07F 15/00; C07F 11/00; C07F 7/24; C07C 49/14

[52] U.S. Cl. .......................... 556/40; 556/57; 556/81; 556/117; 564/271; 564/278; 564/279

[58] Field of Search .............. 556/146, 40, 148, 57, 556/81, 117; 564/271, 278, 279

[56] References Cited

U.S. PATENT DOCUMENTS

| | | | |
|---|---|---|---|
| 2,801,196 | 7/1957 | Doerr | 148/23 |
| 3,301,688 | 1/1967 | Simpolaar | 106/1 |
| 3,388,141 | 6/1968 | Berenbaum | 260/439 |
| 4,654,053 | 3/1987 | Sievers et al. | 55/68 |
| 4,905,790 | 8/1990 | Norman | 564/278 |

OTHER PUBLICATIONS

Air Products and Chemicals, Inc. Patent Application, Ser. No. 07/502,092, filed on 3/30/90 entitled, "Fluxing Agents Comprising B–Diketone and B–Ketoimine Ligands and a Process For Using the Same".

*Primary Examiner*—Arthur C. Prescott
*Assistant Examiner*—Porfirio Nazario
*Attorney, Agent, or Firm*—Keith D. Gourley; James C. Simmons; William F. Marsh

[57] ABSTRACT

A process for the vapor-phase synthesis of non-adduct volatile fluorinated and non-fluorinated metal-ligand complexes comprising contacting a $\beta$-diketone or $\beta$-ketoimine ligand with an inert carrier gas to vaporize the ligand, reacting the vaporized ligand with a metal species at a temperature sufficient to form the metal-ligand complex and recovering the metal-ligand complex by sublimation. The process is conducted in the absence of solvent thereby providing pure non-adduct metal-ligand complexes. Such complexes are particularly suited for specialty applications requiring use of high purity compounds.

43 Claims, No Drawings

SYNTHESIS OF VOLATILE FLUORINATED AND NON-FLUORINATED METAL-BETA-KETONATE AND METAL-BETA-KETOIMINATO COMPLEXES

TECHNICAL FIELD

This invention relates to a process for preparing volatile fluorinated and non-fluorinated metal-$\beta$-ketonate and metal-$\beta$-ketoiminato complexes via a vapor-solid reaction of a $\beta$-diketone or $\beta$-ketoimine ligand and a metal species.

BACKGROUND OF THE INVENTION

Volatile metal-$\beta$-diketonate and metal-$\beta$-ketoiminato complexes are used in a wide range of applications including trace metal analysis by gas chromatography, studies of the stereochemistry and isomerization of metal complexes, ligand exchange, gasoline antiknock additives and in the vapor deposition of metals.

Metal $\beta$-diketonate complexes used as metal precursors in chemical vapor deposition processes must be of high purity and guaranteed volatility. The demand for high purity and guaranteed volatility is particularly acute in the electronics industry. Metal-ligand complexes are typically sold in the form of the hydrated or solvated adduct. While some specialty chemical manufacturers offer anhydrous metal-$\beta$-ketonate complexes, these complexes are typically prepared by utilizing a non-aqueous solvent such as methanol wherein the complex is sold in the form of a solvated adduct (i.e., $M(L)_2 \cdot MeOH$). These adduct complexes often do not satisfy the stringent requirements imposed by some sensitive processes and are difficult to isolate requiring cumbersome purification schemes involving recrystallization.

Attempts have been made to effect the liquid-phase condensation of a primary amine or a primary diamine with a ligand represented by Formula I:

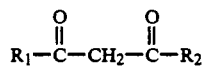

In substances in which $R_1$ and $R_2$ are not both fluorocarbon groups, the literature reports that one of the ketone oxygens can be replaced with a nitrogen atom from an amine group by direct Schiff-base liquid-phase condensation between an appropriate $\beta$-diketone and an amine. Additionally, the corresponding metal complex can be synthesized by chelation to a metal species. See A. E. Martell, et al., *J. Inorg. Chem.*, Volume 5, pp. 170–81 (1958).

As reported by Sievers, et al., in *J. Inorg. Nucl. Chem.*, Volume 32, pp. 1895–906 (1970), ligands according to Formula I wherein both $R_1$ and $R_2$ are perfluoroalkyl and in which an oxygen atom has been replaced with an amine to form a ketoimine, have not been obtainable utilizing liquid-phase or vapor-phase conditions.

A need exists in the art for a process capable of preparing highly volatile metal-ligand complexes in high purity wherein the ligand is a $\beta$-diketone or $\beta$-ketoimine, each of which may also be partially or fully fluorinated. Unfortunately, typical liquid phase processes for preparing such metal-ligand complexes have fallen short of providing the broad range of structures and level of purity required in many current applications such as those employed in the electronics industry.

SUMMARY OF THE INVENTION

The present invention relates to a vapor-phase process for preparing pure, volatile metal-$\beta$-ketonate and metal-$\beta$-ketoiminato complexes in their non-adduct form. The process comprises contacting a $\beta$-diketone or $\beta$-ketoimine ligand with an inert carrier gas to vaporize the ligand, reacting the vaporized ligand with a metal species at a temperature sufficient to form the metal-ligand complex and recovering the metal-ligand complex by sublimation. This vapor phase process overcomes many of the disadvantages associated with liquid phase processes and affords access to a broader range of metal-ligand complexes. Moreover, such complexes are isolated in their non-solvated form and the process does not require use of liquid solvents and basic catalysts.

$\beta$-diketone and $\beta$-ketoimine ligands suitable for use in the claimed process are represented by the structural formula:

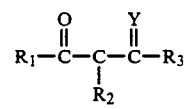

wherein
$R_1$ and $R_3$ are independently selected from a linear or branched alkyl or alkenyl group having from 1 to about 8 carbon atoms, each of which can optionally be partially or fully fluorinated;
$R_2$ is a hydrogen atom, a linear or branched alkyl or alkenyl group having from 1 to about 8 carbon atoms, each of which can optionally be partially or fully fluorinated; and
Y is selected from an oxygen atom; N—$R_4$ wherein $R_4$ is selected from an alkyl, aryl, aralkyl or hydroxyalkyl group having from 1 to about 10 carbon atoms, each of which can optionally be partially or fully fluorinated; or Y is

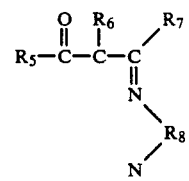

wherein
$R_5$, $R_6$ and $R_7$ are independently selected from a linear or branched alkyl or alkenyl group having from 1 to about 8 carbon atoms, each of which can optionally be partially or fully fluorinated and
$R_8$ is a linear or branched alkylene, alkenylene, phenylene, alkylphenylene or hydroxyalkylene group having from 1 to about 8 carbon atoms, each of which can also be partially or fully fluorinated.

The above-mentioned formula I represents three distinct types of ligands which are each suitable for practicing the present invention. Each of the three types is characterized by the definition of the Y group. When Y is an oxygen atom, the ligand is a $\beta$-diketone. When Y is N—$R_4$, the ligand is a $\beta$-ketoimine ligand. Finally, when Y is represented by Formula II, the ligand comprises two β-ketoimines bridged by an organic functionality.

Metal species suitable for practicing the invention include metal oxides and metal halides. Suitable metal oxides are represented by the formulae MO, MO$_2$, MO$_3$, M$_2$O, and M$_2$O$_3$ and include SnO, Cu$_2$O, CuO, PbO, Y$_2$O$_3$ and CrO$_3$. Suitable metal halides are represented by the formula $M^{+n}(X)^{-n}$, wherein n is 1, 2 or 3 and X is a halogen selected from chlorine, iodine or a bromine atom.

The process of the present invention can optionally be run continuously with minimum operator attendance. The reaction will continue until the limiting reagent has been expended. Production rates in an optimized reactor can potentially be faster than solution-based reactions due to the more favorable kinetics of gas-phase reactions and post-reaction purification procedures are minimized.

DETAILED DESCRIPTION OF THE INVENTION

The present invention pertains to a vapor phase process for preparing pure, highly volatile metal β-ketonate and metal-β-ketoiminato complexes. The process provides several advantages over prior art techniques which are conducted in the liquid phase. For example, the metal-ligand complexes are produced in an adduct-free form in contrast to the complexes formed in solvent-based systems which are usually coordinated with the reaction solvent, typically water or methanol. The process also affords a convenient recovery step wherein the metal-ligand complexes are recovered by sublimation at temperatures wherein the reaction by-products are not condensed out of the process inert atmosphere thereby eliminating tedious recystallization steps typically required in liquid phase processes.

The process for making the metal-ligand complexes of the present invention comprises contacting a β-diketone or β-ketoimine ligand with an inert carrier gas to vaporize the ligand, reacting the vaporized ligand with a metal species at a temperature sufficient to form the desired metal-ligand complex and recovering the metal ligand complex by sublimation.

The highly volatile metal complexes which can optionally be prepared from the above-mentioned process are represented by the formula:

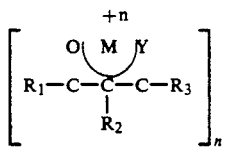

wherein

R$_1$ and R$_3$ are independently selected from a linear or branched alkyl or alkenyl group having from 1 to about 8 carbon atoms, each of which can optionally be partially or fully fluorinated;

R$_2$ is a hydrogen atom, or a linear or branched alkyl or alkenyl group having from 1 to about 8 carbon atoms, each of which can optionally be partially or fully fluorinated; and Y is selected from an oxygen atom; N—R$_4$ wherein R$_4$ is selected from an alkyl, aryl, aralkyl or hydroxyalkyl group having from 1 to about 10 carbon atoms, each of which can optionally be partially or fully fluorinated; or Y is

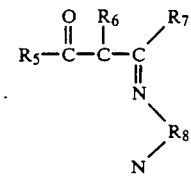

wherein

R$_5$, R$_6$ and R$_7$ are independently selected from a linear or branched alkyl or alkenyl group having from 1 to about 8 carbon atoms, each of which can optionally be partially or fully fluorinated and R$_8$ is a linear or branched alkylene, alkenylene, phenylene, alkylphenylene or hydroxyalkylene group having from 1 to about 8 carbon atoms, each of which can also be partially or fully fluorinated; and M is a metal having a valence, n, which is capable of forming a metal-ligand complex.

Throughout the specification and when interpreting the scope of the appended claims, when reference is made to R$_1$ and R$_3$, such linear or branched alkyl and alkenyl groups shall also contemplate hydroxy alkyl and hydroxy alkenyl groups.

β-diketone and β-ketoimine ligands suitable for practicing the present invention are represented by the formula:

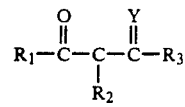

wherein

R$_1$ and R$_3$ are independently selected from a linear or branched alkyl or alkenyl group having from 1 to about 8 carbon atoms, each of which can optionally be partially or fully fluorinated;

R$_2$ is a hydrogen atom, a linear or branched alkyl or alkenyl group having from 1 to about 8 carbon atoms, each of which can optionally be partially or fully fluorinated; and Y is selected from an oxygen atom; N—R$_4$ wherein R$_4$ is selected from an alkyl, aryl, aralkyl or hydroxyalkyl group having from 1 to about 10 carbon atoms, each of which can optionally be partially or fully fluorinated; or Y is

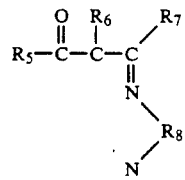

wherein

R$_5$, R$_6$ and R$_7$ are independently selected from a linear or branched alkyl or alkenyl group having from 1 to about 8 carbon atoms, each of which can optionally be partially or fully fluorinated and R$_8$ is a linear or branched alkylene, alkenylene, phenylene, alkylphenylene or hydroxyalkylene group having from 1 to about 8 carbon atoms, each of which can also be partially or fully fluorinated.

Formula II represents three distinct types of ligands which are each suitable for practicing the present invention. Each of the three types is characterized by the definition of the Y group. When Y is an oxygen atom, the ligand is a β-diketone. When Y is N—R₄, the ligand is a β-ketoimine ligand. Finally, when Y is represented by the substituent presented in Formula IIa, the ligand comprises two β-ketoimines bridged by an organic functionality. In a preferred embodiment, R₁ and R₃ are independently selected from a linear or branched alkyl group having from one to four carbon atoms, each of which is non-fluorinated or partially or fully fluorinated.

The non-fluorinated, and partially or fully fluorinated β-diketone ligands suitable for practicing the present invention are represented by the formula:

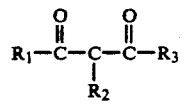

III wherein

R₁ and R₃ are independently selected from a linear or branched alkyl or alkenyl group having from 1 to about 8 carbon atoms, each of which can optionally be partially or fully fluorinated; and R₂ is selected from a hydrogen atom, or a linear or branched alkyl or alkenyl group having from 1 to about 8 carbon atoms, each of which can optionally be partially or fully fluorinated.

The β-diketones represented by Formula III are prepared according to methods well known in the art. The preferred β-diketones include 1,1,1,5,5,5-hexafluoro-2,4-pentanedione, 1,1,1-trifluoro-2,4-pentanedione, 2,2,6,6-tetramethyl-3,5-heptanedione and 1,1,1,5,5,6,6,7,7,7-decafluoro-2,4-heptanedione. In a preferred embodiment, R₁ and R₃ are independently selected from a linear or branched alkyl group having from one to four carbon atoms, which is non-fluorinated or partially or fully fluorinated.

The non-fluorinated and partially or fully fluorinated β-ketoimine ligands of the present invention are represented by the Formula:

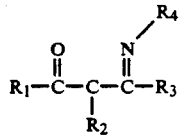

IV wherein

R₁ and R₃ are independently selected from a linear or branched alkyl or alkenyl group having from 1 to about 8 carbon atoms, each of which can optionally be partially or fully fluorinated;

R₂ is a hydrogen atom, or a linear or branched alkyl or alkenyl group having from 1 to about 8 carbon atoms, each of which can optionally be partially or fully fluorinated; and R₄ is selected from an alkyl, aryl, aralkyl or hydroxyalkyl group having from 1 to about 10 carbon atoms, each of which can optionally be partially or fully fluorinated.

A preferred method for preparing the β-ketoimine ligands disclosed in Formula IV, particularly the partially or fully fluorinated β-ketoimine ligands, is disclosed in U.S. patent application Ser. Nos. 270,719 and 283,418, filed on Nov. 14, 1988 and Dec. 12, 1988, respectively, the Specifications which are specifically incorporated by reference herein.

The β-ketoimines are prepared by treating the corresponding β-diketone with potassium hydride under conditions sufficient to produce the potassium salt of the diketone and subsequently reacting the resultant potassium salt of the diketone with a silylchloride such as tert-butyldimethylsilylchloride to produce a silylenolether having the general formula:

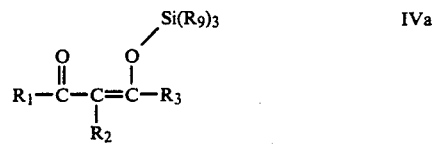

IVa wherein

R₉ is an linear or branched alkyl group having from 1 to about 4 carbon atoms. The silylenolether described above is then treated with a primary monoamine, R₃NH₂, wherein R₃ is defined above, to produce the desired β-ketoimine. In a preferred embodiment, R₁ and R₃ are independently selected from a linear or branched alkyl group having from one to four carbon atoms, which is non-fluorinated or partially or fully fluorinated.

The non-fluorinated and partially or fully flourinated bridged β-ketoimine ligands of the present invention are represented by the Formula:

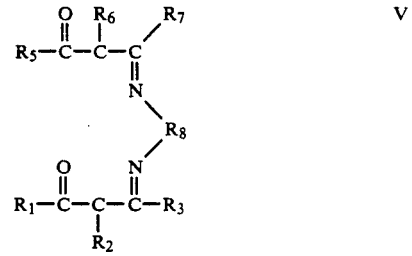

V wherein

R₁ and R₃ are independently selected from a linear or branched alkyl or alkenyl group having from 1 to about 8 carbon atoms, each of which can optionally be partially or fully fluorinated;

R₂ is a hydrogen atom, or a linear or branched alkyl or alkenyl group having from 1 to about 8 carbon atoms, each of which can optionally be partially or fully fluorinated; and R₅, R₆ and R₇ are independently selected from a linear or branched alkyl or alkenyl group having from 1 to about 8 carbon atoms, each of which can optionally be partially or fully fluorinated; and R₈ is a linear or branched alkylene, alkenylene, phenylene, alkylphenylene or hydroxyalkylene group having from 1 to about 8 carbon atoms, each of which can also be partially or fully fluorinated.

A preferred method for preparing the bridged β-ketoimine ligands according to Formula V is described in U.S. patent application Ser. No. 283,418. These ligands are prepared by treating the corresponding β-diketone with potassium hydride under conditions sufficient to form the potassium salt of the diketone and subsequently reacting the resultant potassium salt of the diketone with a silylchloride such as tert-butyldimethylsilylchloride to produce a silylenolether represented by formula IVa. The silylenolether is then treated with two equivalents of a primary diamine, $NH_2R_3NH_2$ wherein $R_3$ is defined above to produce the desired bridged β-ketoimine. In a preferred embodiment, $R_1$ and $R_3$ are independently selected from a linear or branched alkyl group having from one to four carbon atoms, which is non-fluorinated or partially or fully fluorinated.

The ligands of the present invention can exist in two tautomeric forms, keto and enol, the structure of the enol form which is easily understood by those skilled in the art. Reference to the keto form regarding the ligands and metal-ligand complexes of this invention shall also expressly include the corresponding enol form.

The metal species suitable for practicing this invention include metal oxides and metal halides. Suitable metal oxides are represented by the formulae $MO$, $MO_2$, $MO_3$, $M_2O$ and $M_2O_3$. Preferred metal oxides are selected from $SnO$, $Cu_2O$, $CuO$, $PbO$, $Y_2O_3$ and $CrO_3$. Suitable metal halides are represented by the formula $M^{+n}X^{-n}$, wherein n is 1, 2 or 3 and X is a halogen selected from Cl, Br or I. The preferred halogen is a chlorine atom.

The process according to the present invention is conveniently practiced in a conventional multi-stage gas phase reactor. The range of temperatures for operating the process is dependent upon the ligand and metal species chosen for the reaction. Typically, the reaction temperature should not exceed a temperature of about 25° to 50° C. below the decomposition temperature of the reactants to ensure that the desired product does not decompose. This parameter requires some prior knowledge of expected products so that the reaction is not carried out at temperatures that might inhibit product formation or result in product decomposition. However, the decomposition temperature of the ligands of the present invention are easily determined and the optimum temperature for operating the process can be ascertained by those skilled in the art without undue experimentation.

The collection area of the reactor is maintained at temperatures greater than the condensation temperatures of the process by-products ($H_2O$ and acid halides). More particularly, ther collection area is maintained at a temperature at or below the temperature at which the product sublimes from the vapor phase allowing for the collection of the desired metal-ligand complex as a solid. The temperature of the reactor collection area should be well above 100° C. to ensure formation of anhydrous, non-adduct product. When the metal source is a metal halide, a haloacid gas is generated instead of the analogous reaction with metal oxide wherein water is the by-product. Since haloacids in the gas phase typically do not form adducts with metal β-diketonate or β-ketoimine complexes, any potential problems attendant to selection of the appropriate operating temperature within the condensation/collection zone are mitigated.

Inert carrier gases suitable for practicing the process include any gas which is capable of carrying the defined ligands in the vapor phase for subsequent reaction with the metal species. The inert carrier gases must not be capable of reacting with the ligands or metal species. Such gases include argon, nitrogen, helium and perfluorinated hydrocarbons such as Multifluor APF-200 which is commercially available from Air Products and Chemicals, Inc; Allentown, PA. The preferred inert gas is nitrogen.

The following examples are provided to further illustrate various embodiments and are not intended to restrict the scope of the invention. In the following examples, temperatures are set forth uncorrected in degrees Celcius. Unless otherwise indicated, all parts and percentages are by weight. Solvents used were HPLC grade. Tetrahydrofuran (THF) was distilled from calcium hydride under nitrogen and methanol was distilled from magnesium metal under nitrogen. All operations in the preparation of the free ligands or corresponding metal-ligand complexes were carried out using standard Schlenk line techniques described by D. F. Shriver, "The Manipulation of Air Sensitive Compounds", McGraw-hill Publishing Co.

Microanalyses were performed by Schwarzkopf Microanalytical Laboratory, Woodside, NY or Research Services, Air Products and Chemicals, Inc. $^1H$, $^{19}F$ and $^{13}C$ spectra were recorded using an IBM SY-200 and Bruker WH-200 NMR spectrometers.

Examples 1 through 6 illustrate the preparation of metal complexes formed by the reaction of various metal oxides with 1,1,1,5,5,5-hexafluoro-2,4-pentanedione, having the common name, hexafluoroacetylacetone, referred to herein as [HFAC]. The metal-ligand complexes prepared according to Examples 1 through 6 are represented by Formula VI wherein $M^{+n}$ represents the metal, M, having a valence, n which corresponds to the metal of the metal oxide used in the Example. The charge on the metal complex must remain neutral, i.e., if the ligand is diprotonated, then one divalent metal atom such as $Cu^{+2}$ is required.

1,1,1,5,5,5-hexafluoro-2,4-pentanedione
[HFAC]
+n

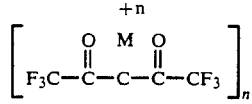

VI

EXAMPLE 1

Preparation of $Cu(Hfac)_2$ 7.5250 grams of cupric oxide ($Cu_2O$), purchased from ALFA Chemical Corporation, 152 Andover Street, Danvers, Mass. 07923, was quantitatively weighed and transferred to a Pyrex brand cylindrical reactor and boat. The boat was placed in a Telemecanique XCK-L tube furnace with TIC control and was heated to 200° C. for 6 hours in order to remove moisture from the system and powder. No additional heat was applied to the exterior regions of the reactor. [HFAC], purchased from Strem Chemicals, Inc., Newburyport, Mass. 10950, was transferred to a Pyrex brand bubbler apparatus. Nitrogen gas at 1 ATM at a flow rate of 0.334 scfh was passed through the bubbler containing the [HFAC] and the resultant [HFAC]/$N_2$ stream was passed through an introduction port and over the bed of $Cu_2O$. The reaction was conducted for a period of 30 minutes under ambient pressure wherein the metal-ligand complex in the form of blue/green crystals formed on the cold regions of the furnace walls. The metal-ligand complex was isolated via sublimation utilizing a condenser maintained at −15° C. Unreacted [HFAC] was recycled for further reaction. The metal-ligand complex had a sublimation point under vacuum of 80° C.

EXAMPLE 2

Preparation of Cu(Hfac)$_2$

The experimental procedure according to Example 1 was utilized with the exception that 8.013 grams of cuprous oxide was utilized. The metal-ligand complex was isolated in the form of blue/green colored crystals having a sublimation point under vacuum of 80° C.

EXAMPLE 3

Preparation of Pb(Hfac)$_2$

The experimental procedure according to Example 1 was utilized with the exception that 12.056 grams of plumbous oxide (PbO) was utilized. The metal ligand complex was isolated in the form of white colored crystals having a sublimation point of <200° C.

EXAMPLE 4

Preparation of Sn(Hfac)$_2$

The experimental procedure according to Example 1 was utilized with the exception that 13.160 grams of stannous oxide (SnO) was utilized. The metal ligand complex was isolated in the form of white colored crystals having a sublimation point of <200° C.

EXAMPLE 5

Preparation of Y(Hfac)$_3$

The experimental procedure according to Example 1 was utilized with the exception that 2.000 grams of yttrium oxide (Y$_2$O$_3$) was utilized; and a process temperature of 260° C. employed. The metal ligand complex was isolated in the form of white colored crystals having a sublimation point of 150° C. under dynamic vacuum and 200° C. under ambient conditions.

EXAMPLE 6

Preparation of Cr(Hfac)$_3$ from CrO$_3$

The experimental procedure according to Example 1 was utilized with the exception that 1.000 grams of chrome oxide (CrO$_3$) was utilized. The metal ligand complex was isolated in the form of orange/red colored crystals having a sublimation point of <200° C.

Metal-ligand complexes of diverse structure may be prepared according to the process of the present invention. Representative ligands are disclosed below wherein the chemical structure and both the IUPAC and abbreviated names of the ligands are provided. The metal-ligand complexes have the structure corresponding to the ligand used in the process with M representing a metal having a valence +n. The charge on the metal complex must remain neutral, i.e., if the ligand is diprotonated, then one divalent metal atom such as Cu$^{+2}$ is required.

4-(2,2,2-trifluoroethyl)-imino-1,1,1,5,5,5-hexafluoro-2-pentanone (H)NONA-F[TFEA]

$$F_3C-\overset{O}{\underset{\|}{C}}-CH_2-\overset{N-CH_2}{\underset{\|}{C}}-CF_3$$

5-(2,2,2-trifluoroethyl)imino-1,1,1,2,2,6,6,6-octafluoro-3-hexanone (H)UNDECA-F[TFEA]

$$CF_3CF_2-\overset{O}{\underset{\|}{C}}-CH_2-\overset{N-CH_2}{\underset{\|}{C}}-CF_3$$

6-(2,2,2-trifluoroethyl)imino-1,1,1,2,2,3,3,7,7,7-decafluoro-4-heptanone (H)TRIDECA-F[TFEA]

$$CF_3CF_2CF_2-\overset{O}{\underset{\|}{C}}-CH_2-\overset{N-CH_2}{\underset{\|}{C}}-CF_3$$

4-(2-hydroxyethyl)imino-1,1,1,5,5,5-hexafluoro-2-pentanone (H)HEXA-F[EOA]

$$F_3C-\overset{O}{\underset{\|}{C}}-CH_2-\overset{N-CH_2}{\underset{\|}{C}}-CF_3\ \ \ CH_2OH$$

4-(phenyl)imino-1,1,1,5,5,5,-hexafluoro-2-pentanone (H)HEXA-F[AN]

$$F_3C-\overset{O}{\underset{\|}{C}}-CH_2-\overset{N-\text{Ph}}{\underset{\|}{C}}-CF_3$$

1,2-di-[4-imino-1,1,1,5,5,5-hexafluoro-2-pentanone]ethane (H$_2$)DODECA-F[EDA]

$$CF_3-\underset{OH}{\overset{|}{C}}=CH-\overset{N}{\underset{\|}{C}}-CF_3$$
$$\qquad\qquad\qquad\ \ \ \diagdown CH_2$$
$$\qquad\qquad\qquad\qquad\ \ \ |\ CH_2$$
$$CF_3-\underset{OH}{\overset{|}{C}}=CH-\overset{N}{\underset{\|}{C}}-CF_3$$

1,2-di-[5-imino-1,1,1,2,2,6,6,6-octafluoro-3-hexanone]ethane (H$_2$)HEXADECA-F[EDA]

$$CF_3CF_2-\underset{OH}{\overset{|}{C}}=CH-\overset{N}{\underset{\|}{C}}-CF_3$$
$$\qquad\qquad\qquad\qquad\ \diagdown CH_2$$
$$\qquad\qquad\qquad\qquad\qquad |\ CH_2$$
$$CF_3CF_2-\underset{OH}{\overset{|}{C}}=CH-\overset{N}{\underset{\|}{C}}-CF_3$$

1,2,-di-[6-imino-1,1,1,2,2,3,3,7,7,7,-decafluoro-4-heptanone]ethane (H$_2$EiCOSA-F[EDA]

$$CF_3CF_2CF_2-\underset{OH}{\overset{|}{C}}=CH-\overset{N}{\underset{\|}{C}}-CF_3$$
$$\qquad\qquad\qquad\qquad\qquad\diagdown CH_2$$
$$\qquad\qquad\qquad\qquad\qquad\quad |\ CH_2$$
$$CF_3CF_2CF_2-\underset{OH}{\overset{|}{C}}=CH-\overset{N}{\underset{\|}{C}}-CF_3$$

Bis[4(methylene)imino-1,1,1,5,5,5-hexafluoro-2-pentanone]methane (H$_2$)DODECA-F[PDA]

-continued

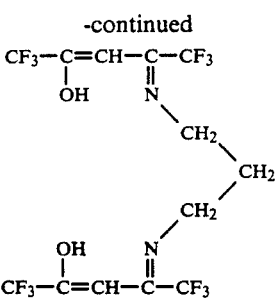

Bis[4-(methylene)imino-1,1,1,5,5,5-hexafluoro-2-pentanone]methanol
(H₂)DODECA-F[POA]

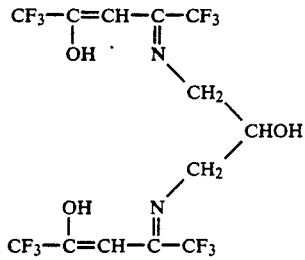

The present invention for the vapor phase synthesis of pure, non-adduct volatile metal β-ketonate and metal-β-ketoiminato complexes provides several advantages over prior art liquid phase, solvent-based processes in that the process affords access to a broader range of metal-ligand complexes, the complexes are isolated in the non-solvated form and the use of basic catalysts is eliminated. Moreover, the process can optionally be run continuously with minimum operator attendance. The reaction will continue until the limiting reagent has been expended. Production rates in an optimized reactor can potentially be faster than solution-based reactions due to the more favorable kinetics of gas-phase reactions and the elimination of post-reaction purification procedures.

Having thus described the present invention, what is now deemed appropriate for Letters Patent is set out in the following appended claims.

We claim:

1. A process for preparing a metal-ligand complex comprising: contacting a β-diketone or β-ketoimine ligand with an inert carrier gas to vaporize the ligand; reacting the vaporized ligand with a metal species at a temperature sufficient to form the metal-ligand complex; and recovering the metal-ligand complex by sublimation.

2. The process according to claim 1 wherein the ligand is represented by the structural formula:

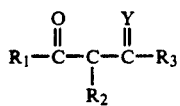

wherein
$R_1$ and $R_3$ are independently selected from a linear or branched alkyl or alkenyl group having from 1 to about 8 carbon atoms, each of which can optionally be partially or fully fluorinated;
$R_2$ is a hydrogen atom, a linear or branched alkyl or alkenyl group having from 1 to about 8 carbon atoms, each of which can optionally be partially or fully fluorinated; and Y is selected from an oxygen atom; N—$R_4$ wherein $R_4$ is selected from an alkyl, aryl, aralkyl or hydroxyalkyl group having from 1 to about 10 carbon atoms, each of which can optionally be partially or fully fluorinated, or Y is

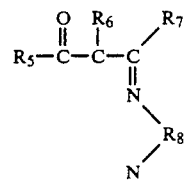

wherein
$R_5$, $R_6$ and $R_7$ are independently selected from a linear or branched alkyl or alkenyl group having from 1 to about 8 carbon atoms, each of which can optionally be partially or fully fluorinated and
$R_8$ is a linear or branched alkylene, alkenylene, phenylene, alkylphenylene or hydroxyalkylene group having from 1 to about 8 carbon atoms, each of which can also be partially or fully fluorinated.

3. The process according to claim 2 wherein the metal species is a metal oxide represented by the formulae MO, MO₂, MO₃, M₂O, and M₂O₃.

4. The process according to claim 3 wherein the metal oxide is selected from SnO, Cu₂O, CuO, PbO, Y₂O₃ and CrO₃.

5. The process according to claim 2 where the metal species is a metal halide represented by the formula $M^{n+}(X^-)n$, wherein n is 1, 2 or 3 and X is a chlorine, bromine or iodine atom.

6. The process according to claim 5 wherein X is a chlorine atom.

7. The process according to claim 2 wherein $R_1$ and $R_3$ are independently selected from a linear or branched alkyl group having from 1 to 4 carbon atoms.

8. The process according to claim 2 wherein $R_1$ and $R_3$ are independently selected from a linear or branched alkyl group having from 1 to about 4 carbon atoms which is partially or fully fluorinated.

9. A process for preparing a metal-ligand complex comprising: contacting a β-diketone ligand represented by the formula:

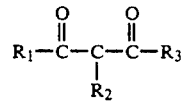

wherein
$R_1$ and $R_3$ are independently selected from a linear or branched alkyl or alkenyl group having from 1 to about 8 carbon atoms, each of which can optionally be partially or fully fluorinated; and
$R_2$ is selected from a hydrogen atom, a linear or branched alkyl or alkenyl group having from 1 to about 8 carbon atoms, each of which can optionally be partially or fully fluorinated; with an inert carrier gas to vaporize the ligand; reacting the vaporized ligand with a metal species at a temperature sufficient to form the metal-ligand complex; and recovering the metal-ligand complex by sublimation.

10. The process according to claim 9 wherein the metal species is a metal oxide represented by the formulae MO, $MO_2$, $MO_3$, $M_2O$, and $M_2O_3$.

11. The process according to claim 10 wherein the metal oxide is selected from SnO, $Cu_2O$, CuO, PbO, $Y_2O_3$ and $CrO_3$.

12. The process according to claim 2 where the metal species is a metal halide represented by the formula $M^{n+}(X^-)n$, wherein n is 1, 2 or 3 and X is a chlorine, bromine or iodine atom.

13. The process according to claim 12 wherein X is a chlorine atom.

14. The process according to claim 9 wherein $R_1$ and $R_3$ are independently selected from a linear or branched alkyl group having from 1 to 4 carbon atoms.

15. The process according to claim 9 wherein the ligand is 1,1,1,5,5,5-hexafluoro-2,4-pentanedione.

16. The process according to claim 9 wherein the ligand is 1,1,1-trifluoro-2,4-pentanedione.

17. The process according to claim 9 wherein the ligand is 2,2,6,6-tetramethyl-3,5-heptanedione.

18. The process according to claim 9 wherein the ligand is 1,1,1,5,6,6,7,7,7-decafluoro-2,4-heptanedione.

19. The process according to claim 9 wherein $R_1$ and $R_3$ are independently selected from a linear or branched alkyl group having from 1 to about 4 carbon atoms which is partially or fully fluorinated.

20. A process for preparing a metal-ligand complex comprising: contacting a β-ketoimine ligand represented by the formula:

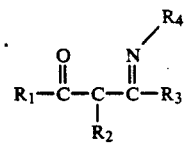

$R_1$ and $R_3$ are independently selected from a linear or branched alkyl or alkenyl group having from 1 to about 8 carbon atoms, each of which can optionally be partially or fully fluorinated;

$R_2$ is a hydrogen atom, or a linear or branched alkyl or alkenyl group having from 1 to about 8 carbon atoms, each of which can optionally be partially or fully fluorinated; and $R_4$ is selected from an alkyl, aryl, aralkyl or hydroxyalkyl group having from 1 to about 10 carbon atoms, each of which can optionally be partially or fully fluorinated;

with an inert carrier gas to vaporize the ligand; reacting the vaporized ligand with a metal species at a temperature sufficient to form the metal-ligand complex, and recovering the metal-ligand complex by sublimation.

21. The process according to claim 20 wherein the metal species is a metal oxide represented by the formulae MO, $MO_2$, $MO_3$, $M_2O$, and $M_2O_3$.

22. The process according to claim 21 wherein the metal oxide is selected from SnO, $Cu_2O$, CuO, PbO, $Y_2O_3$ and $CrO_3$.

23. The process according to claim 20 where the metal species is a metal halide represented by the formula $M^{n+}(X^-)n$, wherein n is 1, 2 or 3 and X is a chlorine, bromine or iodine atom.

24. The process according to claim 23 wherein X is a chlorine atom.

25. The process according to claim 20 wherein $R_1$ and $R_3$ are independently selected from a linear or branched alkyl group having from 1 to 4 carbon atoms.

26. The process according to claim 25 wherein $R_1$ and $R_3$ are independently selected from a linear or branched alkyl group having from 1 to about 4 carbon atoms which is partially or fully fluorinated.

27. The process according to claim 20 wherein the ligand is 4-(2,2,2-trifluoroethyl)imino-1,1,1,5,5,5-hexafluoro-2-pentanone.

28. The process according to claim 20 wherein the ligand is 5-(2,2,2-trifluoroethyl)imino-1,1,1,2,2,6,6,6,-octafluoro-3-hexanone.

29. The process according to claim 20 wherein the ligand is 6-(2,2,2-trifluoroethyl)imino-1,1,1,2,2,3,3,7,7,7-decafluoro-4-heptanone.

30. The process according to claim 20 wherein the ligand is 4-(2-hydroxyethyl)imino-1,1,1,5,5,5-hexafluoro-2-pentanone.

31. The process according to claim 20 wherein the ligand is 4-(phenyl)imino-1,1,1,5,5,5-hexafluoro-2-pentanone.

32. A process for preparing a metal-ligand complex comprising contacting a ligand represented by the formula:

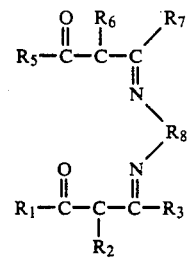

wherein
$R_1$ and $R_3$ are independently selected from a linear or branched alkyl or alkenyl group having from 1 to about 8 carbon atoms, each of which can optionally be partially or fully fluorinated;

$R_2$ is a hydrogen atom, or a linear or branched alkyl or alkenyl group having from 1 to about 8 carbon atoms, each of which can optionally be partially or fully fluorinated;

$R_5$, $R_6$ and $R_7$ are independently selected from a linear or branched alkyl or alkenyl group having from 1 to about 8 carbon atoms, each of which can optionally be partially or fully fluorinated; and $R_8$ is a linear or branched alkylene, alkenylene, phenylene, alkylphenylene or hydroxyalkylene group having from 1 to about 8 carbon atoms, each of which can optionally be partially or fully fluorinated;

with an inert carrier gas to vaporize the ligand; reacting the vaporized ligand with a metal species at a temperature sufficient to form the metal-ligand complex, and recovering the metal-ligand complex by sublimation.

33. The process according to claim 32 wherein the metal species is a metal oxide represented by the formulae MO, $MO_2$, $MO_3$, $M_2O$, and $M_2O_3$.

34. The process according to claim 33 wherein the metal oxide is selected from SnO, $Cu_2O$, CuO, PbO, $Y_2O_3$ and $CrO_3$.

35. The process according to claim 32 where the metal species is a metal halide represented by the formula $M^{n+}(X^-)n$, wherein n is 1, 2 or 3 and X is a chlorine, bromine or iodine atom.

36. The process according to claim 35 wherein X is a chlorine atom.

37. The process according to claim 32 wherein $R_1$ and $R_3$ are independently selected from a linear or branched alkyl group having from 1 to 4 carbon atoms.

38. The process according to claim 32 wherein $R_1$ and $R_3$ are independently selected from a linear or branched alkyl group having from 1 to about 4 carbon atoms which is partially or fully fluorinated.

39. The process according to claim 32 where the ligand is 1,2-di[4-imino-1,1,1,5,5,5-hexafluoro-2-pentanone]ethane.

40. The process according to claim 32 wherein the ligand is 1,2-di[5-imino-1,1,1,2,2,6,6-octafluoro-3-hexanone]ethane.

41. The process according to claim 32 wherein the ligand is 1,2-di-[6-imino-1,1,1,2,2,3,3,7,7,7-decafluoro-4-heptanone]ethane.

42. The process according to claim 32 wherein the ligand is Bis[4-methylene)imino-1,1,1,5,5,5-hexafluoro-2-pentanone]methane.

43. The process according to claim 32 wherein the ligand is Bis[4-methylene)imino-1,1,1,5,5,5-hexafluoro-2-pentanone]methanol.

* * * * *

UNITED STATES PATENT AND TRADEMARK OFFICE
CERTIFICATE OF CORRECTION

PATENT NO. : 5,028,724
DATED : July 2, 1991
INVENTOR(S) : Ivankovits et al.

It is certified that error appears in the above-identified patent and that said Letters Patent is hereby corrected as shown below:

Column 8, line 35, delete
"1,1,1,5,5,5-hexafluoro-2,4-pentanedione [HFAC]

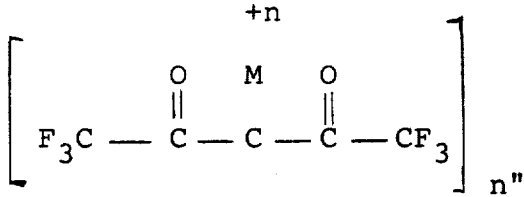

n"

and insert
-- 1,1,1,5,5,5-hexafluoro-2,4-pentanedione [HFAC]

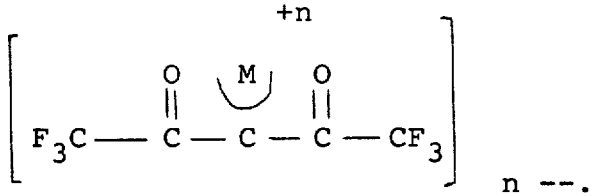

n --.

UNITED STATES PATENT AND TRADEMARK OFFICE
CERTIFICATE OF CORRECTION

PATENT NO. : 5,028,724

DATED : July 2, 1991

INVENTOR(S) : Ivankovits, et al.

It is certified that error appears in the above-identified patent and that said Letters Patent is hereby corrected as shown below:

Column 13, line 39, insert -- wherein -- immediately following the formula.

Signed and Sealed this

Twenty-ninth Day of September, 1992

Attest:

DOUGLAS B. COMER

Attesting Officer   Acting Commissioner of Patents and Trademarks